(12) United States Patent
McLeish (10) Patent No.: US 10,667,832 B2
(45) Date of Patent: Jun. 2, 2020

(54) MEDICAL RETRIEVAL DEVICES AND RELATED METHODS

(71) Applicant: Boston Scientific Scimed, Inc., Maple Grove, MN (US)

(72) Inventor: Eric D. McLeish, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 281 days.

(21) Appl. No.: 15/670,887

(22) Filed: Aug. 7, 2017

(65) Prior Publication Data

US 2018/0042625 A1  Feb. 15, 2018

Related U.S. Application Data

(60) Provisional application No. 62/373,249, filed on Aug. 10, 2016.

(51) Int. Cl.
| | | |
|---|---|---|
| *A61B 17/221* | (2006.01) | |
| *A61B 17/22* | (2006.01) | |
| *A61B 17/3205* | (2006.01) | |
| *A61B 17/00* | (2006.01) | |
| *A61B 17/12* | (2006.01) | |

(52) U.S. Cl.
CPC ...... *A61B 17/221* (2013.01); *A61B 17/22031* (2013.01); *A61B 17/32056* (2013.01); *A61B 17/12109* (2013.01); *A61B 2017/00526* (2013.01); *A61B 2017/2212* (2013.01); *A61B 2017/22072* (2013.01); *A61F 2230/0063* (2013.01)

(58) Field of Classification Search
CPC ... A61B 17/22; A61B 17/221; A61B 17/3205; A61B 17/22031; A61B 17/32056; A61B 17/12109; A61B 2017/2212; A61B 2017/22072; A61B 2017/2215
See application file for complete search history.

(56) References Cited

U.S. PATENT DOCUMENTS

| | | | |
|---|---|---|---|
| 6,872,211 B2 * | 3/2005 | White | A61B 17/22031 606/114 |
| 2002/0068944 A1 | 6/2002 | White et al. | |
| 2002/0091394 A1 | 7/2002 | Reynolds et al. | |
| 2005/0216052 A1 | 9/2005 | Mazzocchi et al. | |
| 2009/0198249 A1 | 8/2009 | Ziegler | |

FOREIGN PATENT DOCUMENTS

| | | |
|---|---|---|
| DE | 102006002531 A1 | 7/2007 |
| WO | WO 00/53106 A1 | 9/2000 |
| WO | WO 01/10290 A1 | 2/2001 |
| WO | WO 05/115257 A1 | 12/2005 |

* cited by examiner

*Primary Examiner* — Vi X Nguyen
(74) *Attorney, Agent, or Firm* — Bookoff McAndrews, PLLC (57) ABSTRACT

A medical device may include a shaft and an end-effector extending distally of the shaft. The end-effector may be expandable between a collapsed configuration and an expanded configuration. The end-effector may include a proximal nose and a distal body. The proximal nose may have a radial dimension smaller than a radial dimension of the distal body in the expanded configuration. The end-effector may include a plurality of legs and a transition point of each leg may be located between the nose and the distal body along a common plane normal to the shaft. The shaft may include proximal ends of the legs wrapped about one another.

20 Claims, 6 Drawing Sheets

MEDICAL RETRIEVAL DEVICES AND RELATED METHODS

CROSS-REFERENCE TO RELATED APPLICATIONS

This patent application claims the benefit of priority under 35 U.S.C. § 119 to U.S. Provisional Patent Application No. 62/373,249, filed Aug. 10, 2016, which is herein incorporated by reference in its entirety.

TECHNICAL FIELD

Various aspects of the present disclosure relate generally to retrieval devices and related methods. More specifically, the present disclosure relates to devices and methods for retrieving objects within a patient.

BACKGROUND

Medical retrieval devices, such as baskets, are often used to remove organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy ("PNCL") procedure. Retrieval devices are also used in lithotripsy and ureteroscopy procedures to treat urinary calculi (e.g., kidney stones) in the ureter of a patient.

Current retrieval devices may include an expandable end-effector having a plurality of legs. However, such legs may be misaligned relative to one another such that the end-effector may fail to properly expand, retrieve objects, or function as desired. The devices and methods of the current disclosure may rectify some of the deficiencies described above or address other aspects of the prior art.

SUMMARY

Examples of the present disclosure relate to, among other things, medical retrieval devices. Each of the examples disclosed herein may include one or more of the features described in connection with any of the other disclosed examples.

In one example, medical device may include a shaft and an end-effector extending distally of the shaft. The end-effector may be expandable between a collapsed configuration and an expanded configuration. The end-effector may include a proximal nose and a distal body. The proximal nose may have a radial dimension smaller than a radial dimension of the distal body in the expanded configuration. The end-effector may include a plurality of legs and a transition point of each leg may be located between the nose and the distal body along a common plane normal to the shaft. The shaft may include proximal ends of the legs wrapped about one another.

Examples of the medical device may additionally or alternatively include any one or more of the following features. The distal body may be spherical in the expanded configuration. The end-effector may include only four legs. The end-effector may be symmetric about an axis of the shaft in the expanded configuration. The nose may include a proximal section having a changing radial dimension in the expanded configuration. The nose may further include an intermediate portion having a changing radial dimension in the expanded configuration, and a distal transition portion. The legs may be coupled to one another via a knot at a distal-most end of the end-effector in the expanded configuration. The end-effector may comprise an atraumatic tip. The end-effector and the shaft may be a one-piece monolithic structure. The legs may be circumferentially equidistant from each other. The end-effector may be comprised of Nitinol. A radius of the distal body may be between about 5 mm and about 10 mm in the expanded configuration. An axial length of the nose may be longer than an axial length of the distal body. The distal transition portion may curve radially outwardly from the nose to the distal body. The transition point of each leg may be located along the distal transition portion.

In a further example, a method of forming a medical device may include positioning a plurality of legs within grooves of a spherical formation die having a proximal stem. The method may further include threading proximal ends of the plurality of legs through a lumen of a mounting ring, positioning the stem within the lumen of the mounting ring, and mounting a flange of a formation rod on the stem. Further, the method may include rotating the formation rod relative to the formation die.

Examples of the method may additionally or alternatively include any one or more of the following features. The method may include placing the proximal ends of the legs in a notch of the formation rod. The method may include moving a collar over the notch and locking the proximal ends of the legs with respect to the formation rod. The method may include tensioning the legs. The method may include including positioning a knot coupling the legs together in a depression on a distal-most end of the formation die.

In a further example, a device may include an end-effector expandable between a collapsed configuration and an expanded configuration. The end-effector may include a proximal nose and a spherical distal body. The nose may have a radial dimension smaller than a radial dimension of the distal body in the expanded configuration. The device may further include a shaft positioned proximally of the end-effector. The end-effector may include a plurality of legs. The nose may include a proximal section having a changing radial dimension in the expanded configuration, an intermediate portion having a changing radial dimension in the expanded configuration, and a distal transition portion. Further, the shaft may include proximal ends of the legs wrapped about one another.

Examples of the medical device may additionally or alternatively include any one or more of the following features. The end-effector may include only four legs. The end-effector may be symmetric about an axis of the shaft in the expanded configuration. The legs may be coupled to one another via a knot at a distal-most end of the end-effector in the expanded configuration. A radius of the distal body may be between about 5 mm and about 10 mm in the expanded configuration.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal."

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical retrieval devices for retrieval of objects within a subject. The medical retrieval device may be coupled to a handle (not shown) and may be delivered through any appropriate insertion device (not shown), such as, e.g., an endoscope.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical retrieval device or insertion device. When used herein, "proximal" refers to a position relatively closer to the exterior of the body or closer to an operator using the medical retrieval device or insertion device. In contrast, "distal" refers to a position relatively further away from the operator using the medical retrieval device or insertion device, or closer to the interior of the body.

Figure 1A:
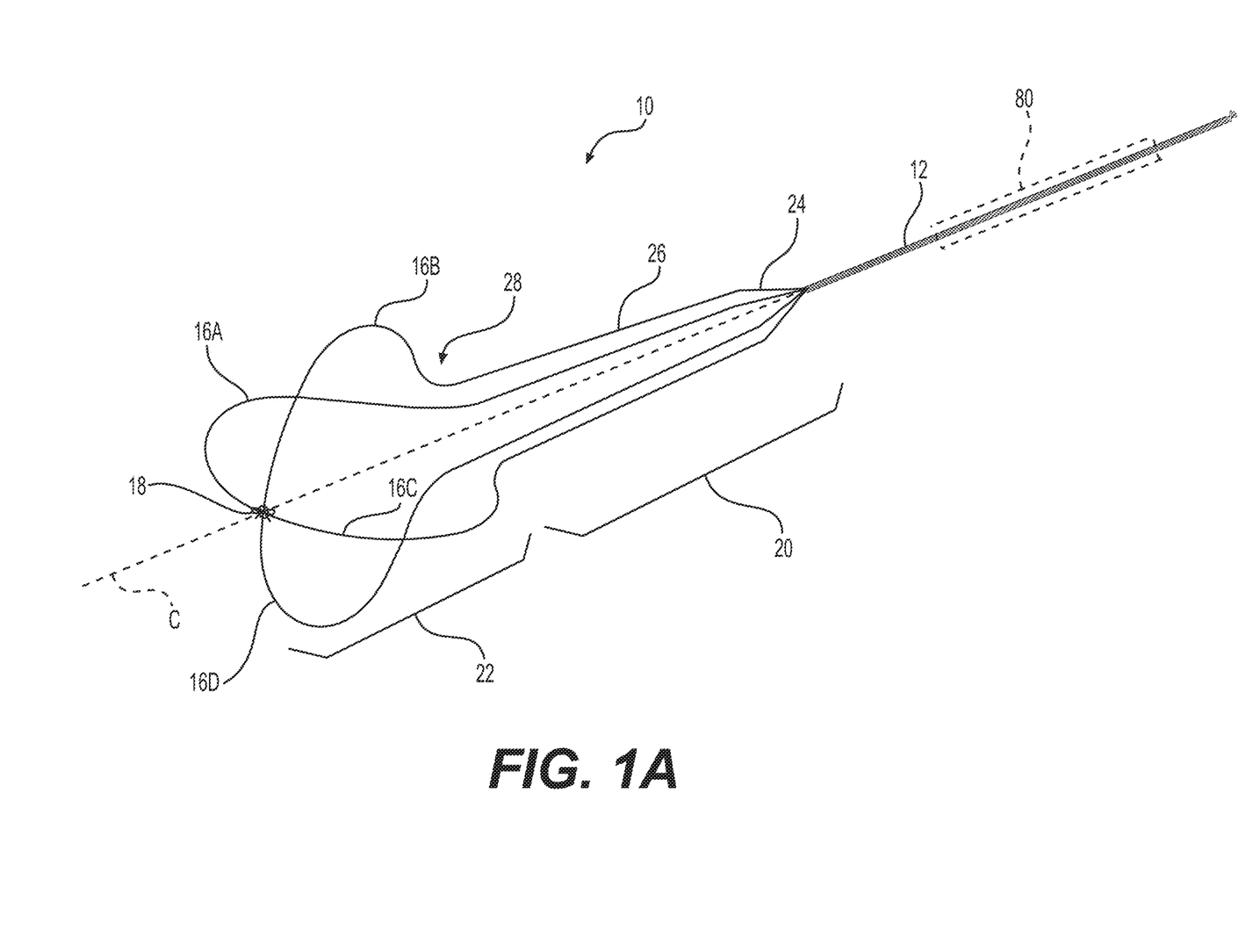
FIG. 1A is a perspective view of an exemplary medical retrieval device having the shaft and an end-effector.
Figure 1B:
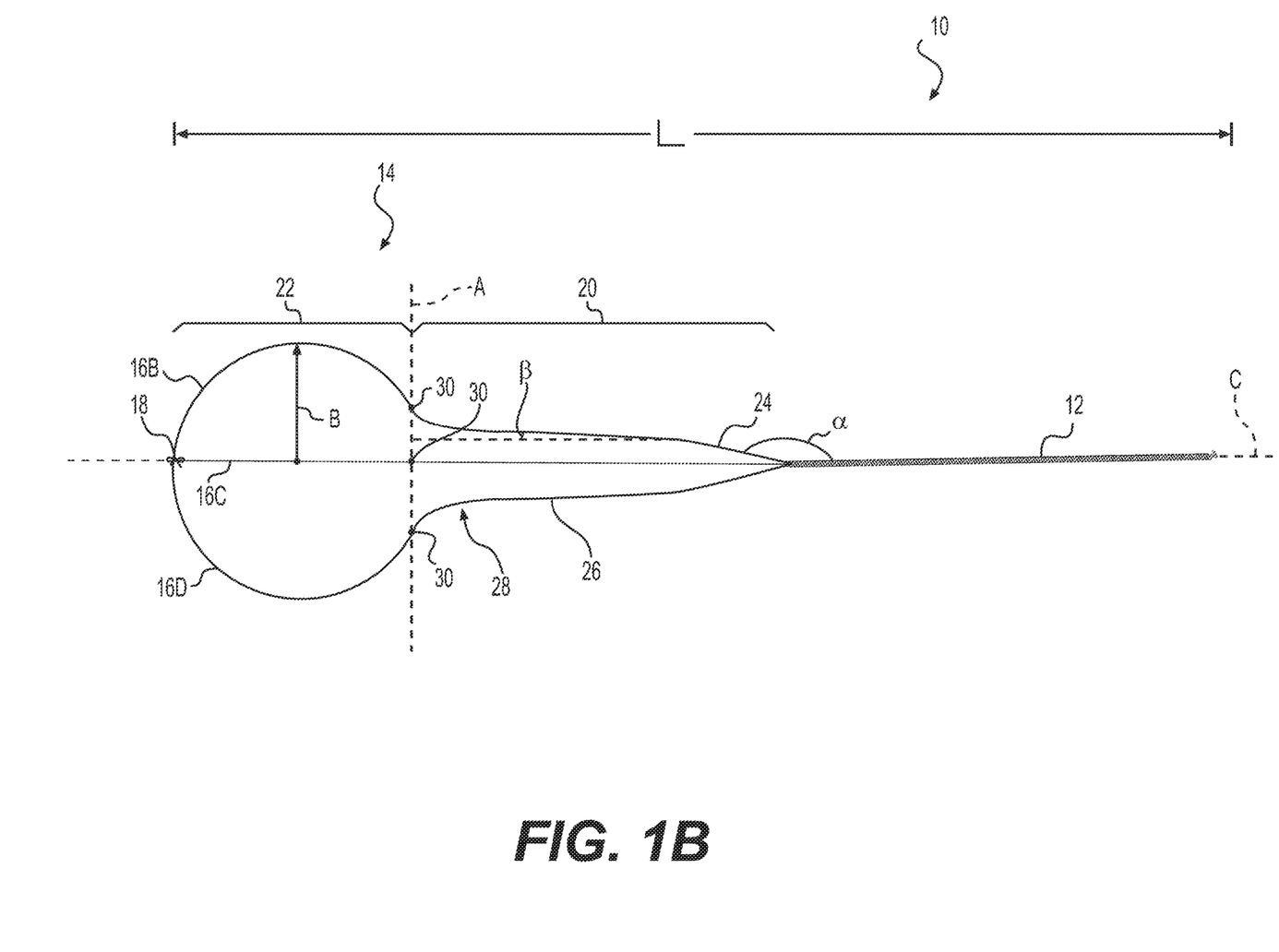
FIG. 1B is a side-view of the exemplary medical retrieval device of FIG. 1A.

FIGS. 1A and 1B illustrate an exemplary medical retrieval device 10, including a shaft 12 terminating in an end-effector 14. As shown, shaft 12 and end-effector 14 may be monolithic. As shown in FIG. 1A, end-effector 14 and shaft 12 are a one-piece monolithic construction. However, in some arrangements, shaft 12 and end-effector 14 may be separate components joined together to form device 10. Device 10 may be a medical basket. As such, end-effector 14 may include a plurality of legs 16A-16D. Legs 16A-16D may be radially expandable from a collapsed state (not shown) within a sheath, sleeve, or lumen of any appropriate insertion device (not shown) towards a radially expanded state, as shown in FIGS. 1A and 1B. As such, device 10 may be self-expandable and may be comprised of any appropriate material such as, e.g., Nitinol. That is, upon the removal of a constraining force provided by a sheath, sleeve, or lumen of an insertion device, legs 16A-16D may automatically radially expand away from one another so as to assume the expanded state, as shown in FIGS. 1A and 1B.

As shown in FIG. 1A, device 10 may include four legs 16A-16D. While four legs 16A-16D are shown, it is understood that a greater or lesser number of legs 16A-16D may be provided based on a desired spacing between adjacent legs 16A-16D, and thereby, a size of openings between adjacent legs 16A-16D. Such adjustments may enable objects of various sizes to be received within and retained by end-effector 14.

Legs 16A-16D may be joined together in any appropriate manner. For example, as shown in FIG. 1A, legs 16A-16D may be joined via knot 18. In some arrangements, legs 16A and 16C may be opposite ends or halves of a single continuous wire or other such elongate flexible member, while legs 16B and 16D may be opposite ends or halves of a single continuous wire or other such elongate flexible member. The members may be tied or otherwise joined together via knot 18 to thereby form a tipless or zero-tip basket, as is known. For example, knot 18 may form an atraumatic tip of minimal profile to reduce any inadvertent tissue trauma. Indeed, with knot 18, end-effector 14 is atraumatic in that the distal-most end of end-effector 14 does not have any significant distal protrusion or outward projection that can poke tissue, pierce tissue, otherwise cause trauma to tissue, or inhibit or hinder capturing of material from within the body of a subject. In some arrangements, however, four (or more) separate and distinct members may be tied or otherwise joined together via knot 18 to form end-effector 14 without departing from the scope of this disclosure.

As shown in FIGS. 1A and 1B, end-effector 14 may have a proximal nose 20 terminating in a body 22. As shown, nose 20 may have a proximal portion 24 adjacent to shaft 12, an intermediate portion 26, and a distal transition portion 28. Proximal portion 24 may have a varied or changing radial dimension or size. For example, proximal portion 24 may taper, angle, or curve radially outwardly in a distal direction. In some arrangements, proximal portion 24 may extend at an angle α of between about 45° and about 75° (e.g., 50°) with respect to shaft 12. Intermediate portion 26 may have a longitudinal length longer than a longitudinal length of proximal portion 24. For example, intermediate portion 26 may have a longitudinal length between about 200% and about 350% longer than proximal portion 24. Indeed, intermediate portion 26 may have a length between about 9 mm and about 11 mm, while proximal portion 24 may have a length between about 4 mm and about 5 mm. As used herein, the terms "about," "substantially," and "approximately," may indicate a range of values within +/−5% of a stated value. Similarly to proximal portion 24, intermediate portion 26 may have a varied or changing radial dimension or size such that intermediate portion 26 may taper, angle, or curve radially outwardly in a distal direction. For example, intermediate portion 26 may extend at an angle β between about 0° and about 10° with respect to an axis parallel to shaft 12. Alternatively, intermediate portion 26 may have a substantially constant radial dimension along the length of intermediate portion 26 such that intermediate portion extends substantially parallel to shaft 12.

As shown in FIGS. 1A and 1B, distal transition portion 28 may be located between intermediate portion 26 of nose 20 and body 22. As shown, distal transition portion 28 may taper, curve, and/or bend radially outwardly from intermediate portion 26 toward body 22. Additionally, each leg 16A-16D may include a transition point 30 (FIG. 1B) at a location between distal transition portion 28 and body 22. As shown, transition point 30 of each leg 16A-16D is located on a common plane A (leg 16A is out of the plane of view in FIG. 1B and would be directly behind leg 16C). As shown in FIG. 1B, plane A is normal (e.g., perpendicular) to a longitudinal axis C of shaft 12.

Body 22 may be spherically shaped and enlarged relative to nose 20. As best shown in FIG. 1B, for example, body 22 may have a radius B of between about 5 mm and about 10 mm in the expanded configuration. As shown in FIGS. 1A and 1B, end-effector 14 may be symmetric about axis C.

Additionally, a total length L of device 10, extending from the proximal-most end of shaft 12 to the distal-most end of body 22, may be between about 9 mm and about 12 mm. In some arrangements, the proximal-most end of shaft 12 may extend all the way to the handle (not shown). In other arrangements, a proximal-most end of shaft 12 may be coupled to an actuation rod, wire, or other such member (not shown) which may be advanced/retracted to cause a likewise advancement of shaft 12, without departing from the scope of this disclosure.

Shaft 12, as shown in FIGS. 1A and 1B may include proximal ends of legs 16A-16D wrapped about one another (e.g., spiraled and/or twisted). Such twisting locks the legs 16A-16D together so as to form shaft 12 without the aid of additional heat shrink materials, tubes, lumens, or the like. That is, device 10 may be free from any material or structure to maintain legs 16A-16D in contact with one another to form shaft 12. However, if desired, an optional sheath 80 may be positioned on or about shaft 12, as described below.

Figure 2A:
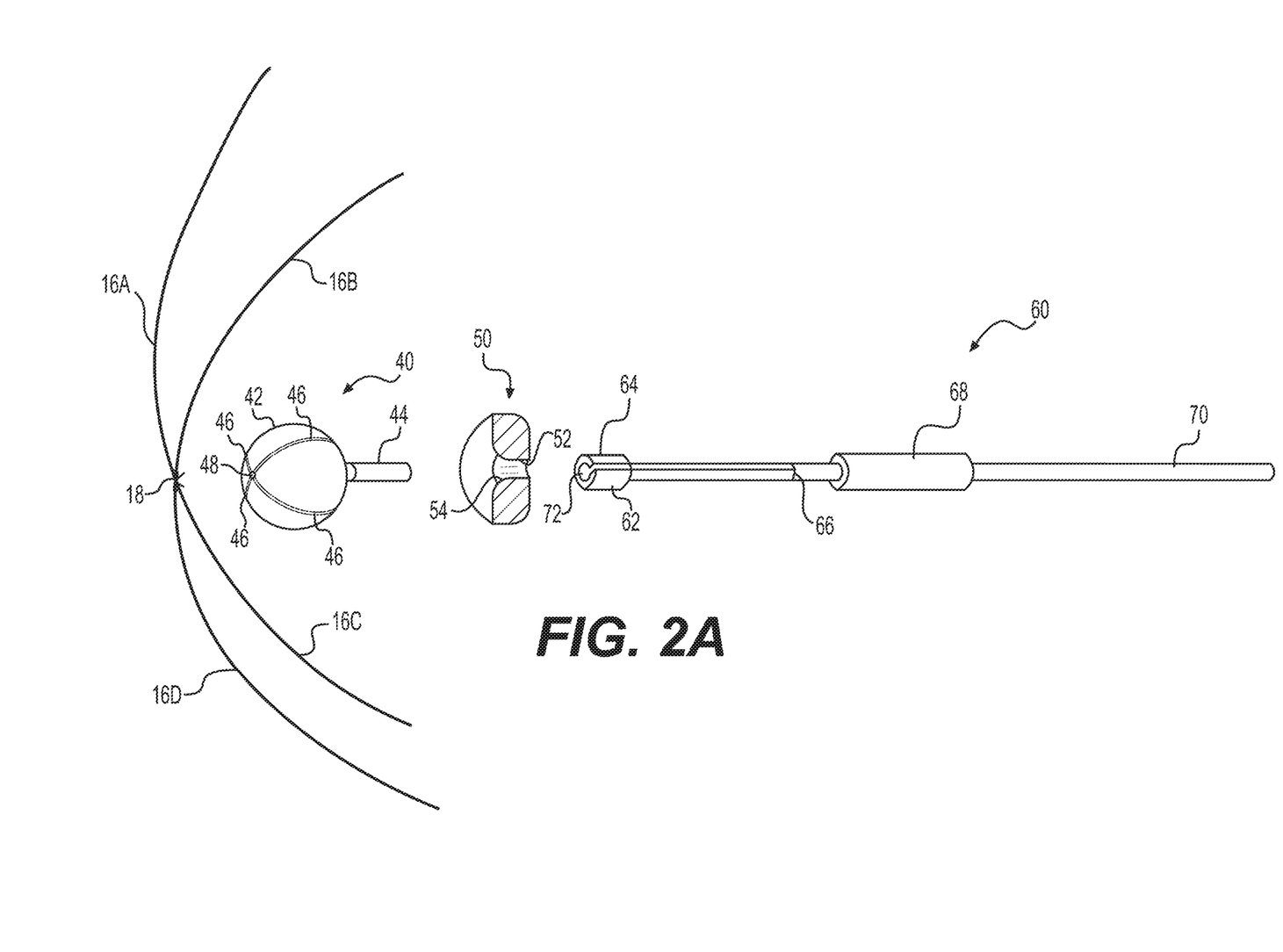
FIGS. 2A-2D illustrate an exemplary system and method of forming the medical retrieval device of FIGS. 1A and 1B, according to aspects of this disclosure.

FIGS. 2A-2D illustrate an exemplary system for, and method of, forming device 10 of FIGS. 1A and 1B. For example, as shown in FIG. 2A, prior to formation of end-effector 14, legs 16A-16D are coupled together via knot 18 and may be positioned adjacent an end-effector formation die 40. For example, legs 16A-16D may be joined by a double overhead loop knot. Die 40 may include a body 42 and a stem 44. As shown, body 42 may be spherically shaped so as to impart a likewise spherical shape to body 22 of end-effector 14 (as shown in FIGS. 1A and 1B). That is, body 42 may have any radial dimension, size, or shape so as to form, mold, bend, fix, or otherwise arrange body 22 of end-effector 14 in the same or corresponding manner. In addition, as shown in FIG. 2A, body 42 may include a plurality of grooves or channels 46 extending about a radially outer surface of body 42 and an opening or depression 48 at a distal-most end face of body 42. Channels 46 may be positioned about body 42 and may be equidistantly spaced therebetween, and may extend from depression 48 toward stem 44. Alternatively, channels 46 may not be equidistantly spaced, if so desired. Channels 46 may have any appropriate depth. For example, channels 46 may have a depth of between about 0.3 mm and about 0.5 mm.

The system for forming device 10 also may have a fixing member or ring 50 having a lumen 52. Lumen 52 may have a radial dimension or size sufficient to receive stem 44 therein, as will be described in further detail below. Additionally, a radially inner surface 54 of lumen 52 may be arcuate or otherwise curved. As such, upon insertion of stem 44 through lumen 52, inner surface 54 may abut or contact a proximal end of body 42. Further, a formation handle or rod 60, having a lumen 72 extending therethrough, may include a flange 62 at a proximal end thereof. Flange 62 may have an enlarged outer radial dimension relative to a body 70 of rod 60. That is, flange 62 may be sized to receive at least a portion of stem 44 therein, as will be described in further detail below. Rod 60 may include a channel or slot 64 extending along a length thereof. For example, as shown in FIG. 2A, slot 64 may extend from the distal-end of flange 62 towards a cut or notch 66 in body 70. Slot 64 may extend through a circumferential side-wall of body 70 to lumen 72. Rod 60 may further include a collar 68. Collar 68 may have a central lumen (not shown) sized to receive body 70 therein. Collar 68 may be slideably disposed on body 70, as will be described in further detail below.

Figure 2B:
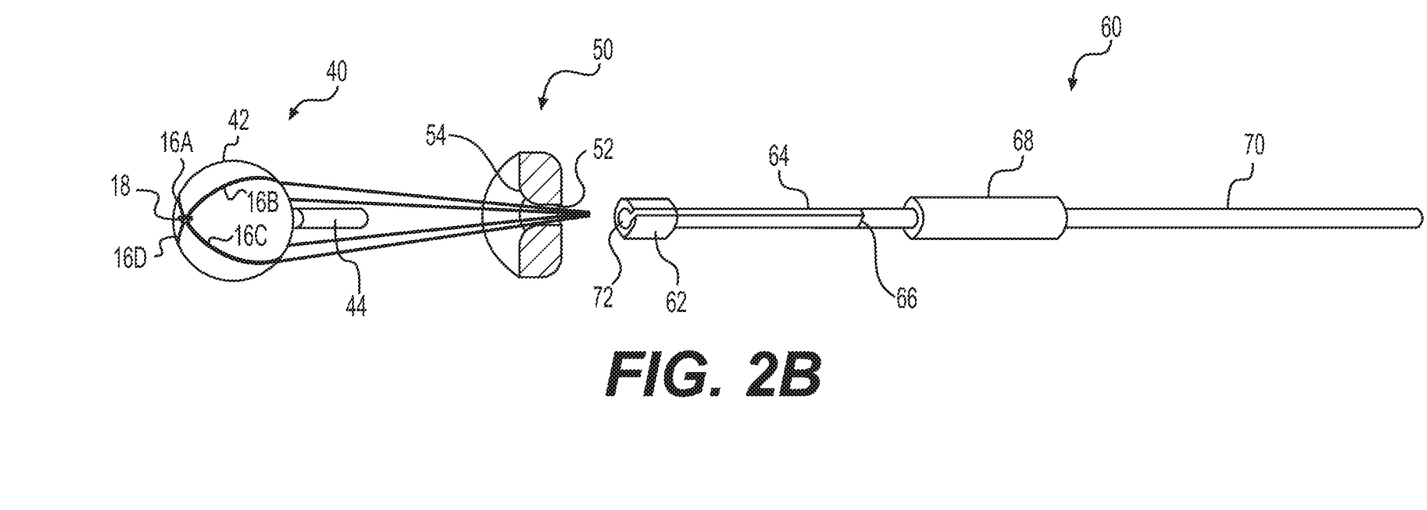
Figure 2C:
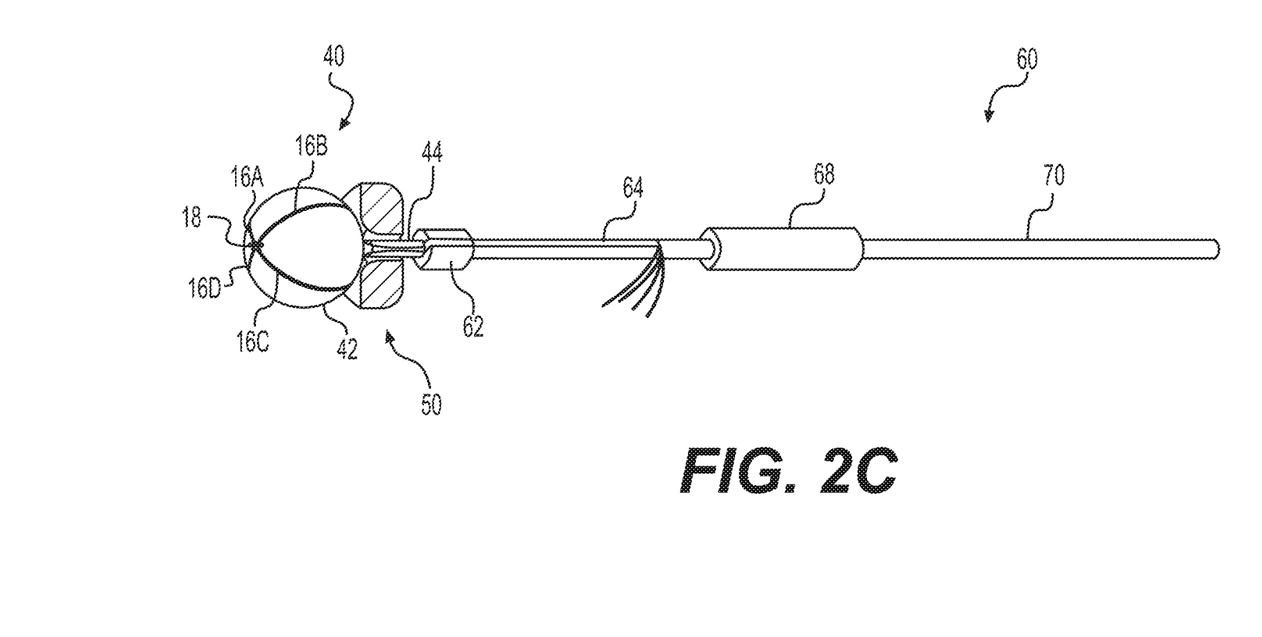

As shown in FIG. 2B, legs 16A-16D may be positioned in channels 46 while knot 18 may be positioned in depression 48 (FIG. 2A). Upon locating legs 16A-16D and knot 18 as shown in FIG. 2B, legs 16A-16D may be pulled or tensioned proximally about body 42 towards ring 50 and through lumen 52. Next, stem 44 may be positioned within lumen 52 of ring 50, as shown in FIG. 2C. As such, a proximal end of body 42 may abut or contact inner surface 54 of ring 50. In such a manner, die 40 may be nested within ring 50. Additionally, as shown in FIG. 2C, stem 44 may be positioned within flange 62 thereby coupling rod 60 to die 40. It is understood, however, that while stem 44 is located within flange 62, flange 62 may still rotate with respect to stem 44, as described below. Proximal ends of legs 16A-16D then may be passed through or along slot 64 of body 70 into lumen 72 (FIG. 2A), towards and through notch 66. That is, proximal ends of legs 16A-16D may be retained within notch 66. In such a manner, legs 16A-16D are fixedly coupled to rod 60. It is understood that tensioning or pulling legs 16A-16D from body 42, through ring 50, through lumen 72, and then through notch 66 of rod 60 maintain the system for forming device 10 together longitudinally.

Figure 2D:
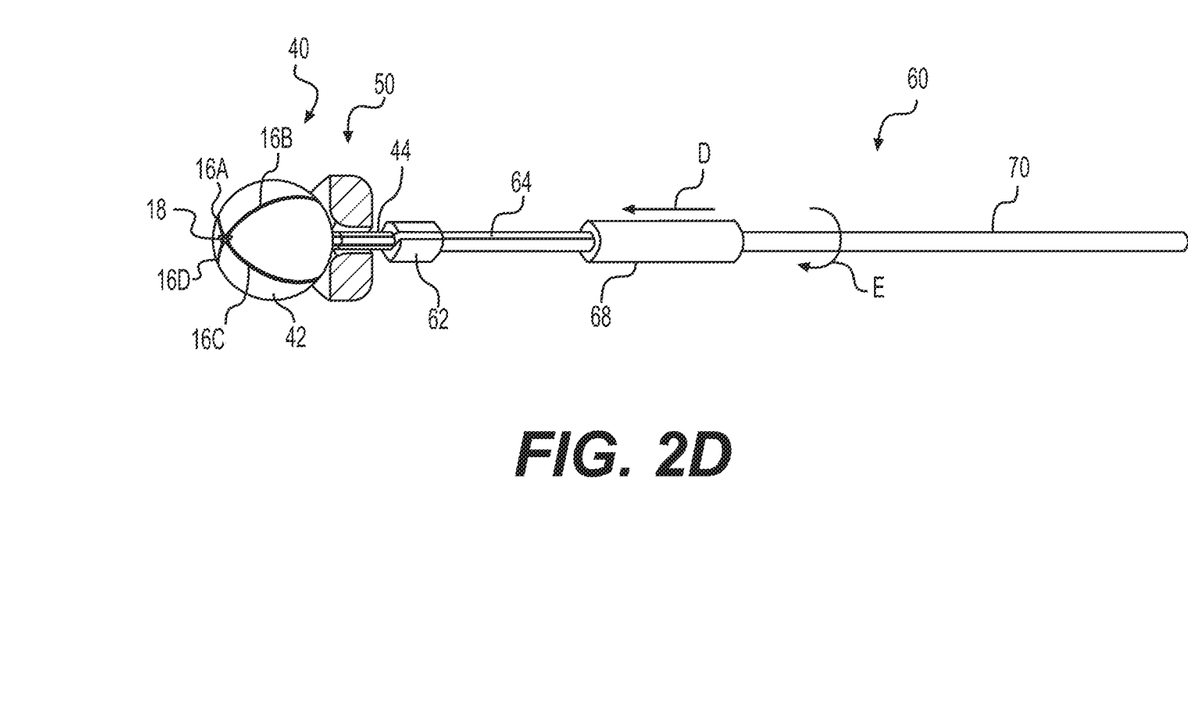

Next, as shown in FIG. 2D, collar 68 may be translated, slid, or otherwise moved distally along body 70 toward die 40. Indeed, as shown, collar 68 may be moved in direction D until collar 68 is positioned over notch 66. In such a manner, collar 68 may pinch or sandwich distal ends of legs 16A-16D between collar 68 and body 70 to maintain legs 16A-16D in a desired position. Next, rod 60 may be rotated in the direction E (e.g., clock-wise) about an axis of body 70, or in a direction opposite (e.g., counter-clock-wise) of direction E, while maintaining die 40 and ring 50 in place. That is, rod 60 may be rotated relative to die 40 and ring 50. Such relative motion may twist, spiral, and/or wrap or twist proximal ends of legs 16A-16D about each other thereby forming shaft 12. That is, rotation of rod 60 relative to die 40 may wrap proximal ends of legs 16A-16D about one another thereby forming device 10 into the shape shown in FIGS. 1A and 1B, and preventing inadvertent movement of legs 16A-16D relative to one another during the forming process. Optionally, device 10 may be heat treated, while still positioned on die 40, ring 50, and rod 60 such that distortion of device 10 (e.g., asymmetric legs and/or failure of transition points of each leg to align along a common plane normal to the longitudinal axis of a shaft) due to heat is avoided while ensuring proper engagement of proximal ends of legs 16A-16D to each other. Also, optionally, a sheath may be placed over shaft 12 to increase a lubriciousness of shaft 12, to form an atraumatic profile for shaft 12, or to prevent or inhibit unfurling, unwinding, or separating of proximal ends of legs 16A-16D during use.

Formation of end-effector 14 in such a manner may exhibit various attributes. First, extension of proximal ends of legs 16A-16D along stem 44 and body 42 may form nose 20 and body 22 of end-effector 14, respectively. For example, placement of portions legs 16A-16D about body 42 may form the likewise shaped body 22, placement of portions of legs 16A-16D along stem 44 may form the likewise shaped nose 20, and rotation of proximal ends of legs 16A-16D may form twisted shaft 12. Additionally, as any heat-treating is performed while device 10 is positioned as shown in FIG. 2D, the system for forming device 10 may prevent distortion of device 10 (e.g., asymmetric legs and/or failure of transition points of each leg to align along a common plane normal to the longitudinal axis of a shaft). Additionally, nose 20 may facilitate opening or expanding of end-effector 14 between the collapsed and expanded states. Indeed, nose 20 may prevent legs 16A-16D from becoming intertwined with one another by maintaining legs spaced radially apart from one another. Additionally, placement of legs 16A-16D in tension during the formation process, as noted above, may tighten and thereby reduce the size of knot 18, thereby forming an increasingly precise end-effector 14 shape.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

I claim:

1. A medical device, comprising:
   a shaft; and
   an end-effector extending distally of the shaft and expandable between a collapsed configuration and an expanded configuration, the end-effector including a proximal nose and a distal body, wherein the proximal nose has a radial dimension smaller than a radial dimension of the distal body in the expanded configuration;
   wherein the end-effector includes a plurality of legs, wherein a transition point of each leg located between the nose and the distal body is located along a common plane normal to the shaft, and wherein the shaft includes proximal ends of the legs wrapped about one another,
   wherein the proximal nose includes a proximal portion, an intermediate portion, and a distal transition portion,
   wherein a changing radial dimension of the intermediate portion is larger than a changing radial dimension of the proximal portion in the expanded configuration, and a changing radial dimension of the distal transition portion is larger than the changing radial dimension of the intermediate portion in the expanded configuration.

2. The medical device of claim 1, wherein the distal body is spherical in the expanded configuration.

3. The medical device of claim 1, wherein the end-effector includes only four legs.

4. The medical device of claim 1, wherein the end-effector is symmetric about an axis of the shaft in the expanded configuration.

5. The medical device of claim 1, wherein the legs are coupled to one another via a knot at a distal-most end of the end-effector in the expanded configuration.

6. The medical device of claim 1, wherein the end-effector comprises an atraumatic tip.

7. The medical device of claim 1, wherein the end-effector and the shaft are a one-piece monolithic structure.

8. The medical device of claim 1, wherein the legs are circumferentially equidistant from each other.

9. The medical device of claim 1, wherein a radius of the distal body is between about 5 mm and about 10 mm in the expanded configuration.

10. A method of forming the medical device of claim 1, comprising:
    positioning the plurality of legs within grooves of a spherical formation die having a proximal stem;
    threading proximal ends of the plurality of legs through a lumen of a mounting ring;
    positioning the stem within the lumen of the mounting ring;
    mounting a flange of a formation rod on the stem; and
    rotating the formation rod relative to the formation die.

11. The method of claim 10, further including placing the proximal ends of the legs in a notch of the formation rod.

12. The method of claim 11, further including moving a collar over the notch and locking the proximal ends of the legs with respect to the formation rod.

13. The method of claim 10, further including tensioning the legs.

14. The method of claim 10, further including positioning a knot coupling the legs together in a depression on a distal-most end of the formation die.

15. The medical device of claim 1, wherein the distal transition portion is between the intermediate portion of the proximal nose and the distal body, and the distal transition portion curves radially outwardly from the intermediate portion towards the distal body.

16. A medical device, comprising:
    an end-effector expandable between a collapsed configuration and an expanded configuration, the end-effector including a proximal nose and a spherical distal body, wherein the nose has a radial dimension smaller than a radial dimension of the distal body in the expanded configuration; and
    a shaft positioned proximally of the end-effector;
    wherein the end-effector includes a plurality of legs, wherein the nose includes a proximal portion having a changing radial dimension in the expanded configuration, an intermediate portion having a changing radial dimension in the expanded configuration, and a distal transition portion, and wherein the changing radial dimension of the intermediate portion is larger than the changing radial dimension of the proximal portion in the expanded configuration, and a changing radial dimension of the distal transition portion is larger than the changing radial dimension of the intermediate portion in the expanded configuration; and
    wherein the shaft includes proximal ends of the legs wrapped about one another.

17. The medical device of claim 16, wherein the end-effector includes only four legs.

18. The medical device of claim 16, wherein the end-effector is symmetric about an axis of the shaft in the expanded configuration.

19. The medical device of claim 16, wherein the legs are coupled to one another via a knot at a distal-most end of the end-effector in the expanded configuration.

20. The medical device of claim 16, wherein a radius of the distal body is between about 5 mm and about 10 mm in the expanded configuration.

* * * * *